(12) United States Patent
Raterink et al.

(10) Patent No.: US 9,919,317 B2
(45) Date of Patent: Mar. 20, 2018

(54) ELECTROEXTRACTION

(71) Applicant: Universiteit Leiden, EZ Leiden (NL)

(72) Inventors: Robert-Jan Raterink, CC Leiden (NL); Peter Lindenburg, CC Leiden (NL); Thomas Hankemeier, RA Leiden (NL)

(73) Assignee: Universiteit Leiden, Leiden (NL)

( * ) Notice: Subject to any disclaimer, the term of this patent is extended or adjusted under 35 U.S.C. 154(b) by 431 days.

(21) Appl. No.: 14/394,895

(22) PCT Filed: Apr. 19, 2013

(86) PCT No.: PCT/NL2013/050285
§ 371 (c)(1),
(2) Date: Oct. 16, 2014

(87) PCT Pub. No.: WO2013/157945
PCT Pub. Date: Oct. 24, 2013

(65) Prior Publication Data
US 2015/0129427 A1 May 14, 2015

Related U.S. Application Data

(60) Provisional application No. 61/635,428, filed on Apr. 19, 2012.

(30) Foreign Application Priority Data

Apr. 19, 2012 (NL) ..................................... 2008662

(51) Int. Cl.
*B03C 5/02* (2006.01)
*B01D 11/04* (2006.01)
(Continued)

(52) U.S. Cl.
CPC ............ *B03C 5/02* (2013.01); *B01D 11/0419* (2013.01); *B01D 57/02* (2013.01); *B01D 61/246* (2013.01);
(Continued)

(58) Field of Classification Search
CPC ..... G01N 2030/0035; G01N 2030/009; G01N 2035/1053
See application file for complete search history.

(56) References Cited

U.S. PATENT DOCUMENTS 3,471,080 A 10/1969 Gray
3,472,080 A 10/1969 Ayvazian
(Continued)

FOREIGN PATENT DOCUMENTS

EP 2461150 6/2012
WO WO 2007/004892 1/2007
(Continued)

OTHER PUBLICATIONS

Kelly et al., "Low-Conductivity Buffers for High-Sensitivity NMR Measurements," J. Am. Chem. Soc. 2002, 124, 12013-12019.*
(Continued)

*Primary Examiner* — Alexander S Noguerola
(74) *Attorney, Agent, or Firm* — Baker & Hostetler LLP

(57) ABSTRACT

The present invention relates to a process for the extraction of analyte compounds from a sample comprising one or more analytes in a donor phase into an acceptor phase, comprising the steps of: a) providing an electrically conductive donor phase comprising the compounds in a first electrically conductive solvent or solvent blend, and an electrode arranged in electrically conductive contact with the donor phase, b) providing an electrically conductive acceptor phase in electrically conductive contact with a second electrode; and c) providing an insulator phase in fluid communication with at least one of the donor phase and the acceptor phase, wherein the insulator phase is immiscible with the donor phase and/or the acceptor phase, and d) (d) applying an electrical field between the first and the second electrode.

16 Claims, 5 Drawing Sheets

(51) Int. Cl.
| | |
|---|---|
| B01D 61/38 | (2006.01) |
| G01N 1/40 | (2006.01) |
| B01D 57/02 | (2006.01) |
| B01D 61/24 | (2006.01) |
| B01D 61/42 | (2006.01) |
| G01N 27/447 | (2006.01) |
| G01N 35/10 | (2006.01) |
| G01N 30/00 | (2006.01) |
| G01N 30/06 | (2006.01) |

(52) U.S. Cl.
CPC .............. *B01D 61/38* (2013.01); *B01D 61/42* (2013.01); *G01N 1/4005* (2013.01); *G01N 27/44756* (2013.01); *G01N 2001/4011* (2013.01); *G01N 2001/4038* (2013.01); *G01N 2030/009* (2013.01); *G01N 2030/062* (2013.01); *G01N 2035/1053* (2013.01)

(56) References Cited

U.S. PATENT DOCUMENTS

| | | |
|---|---|---|
| 3,841,984 A | 10/1974 | Barnes |
| 6,325,908 B1 * | 12/2001 | Imai ................. G01N 27/44782 204/453 |
| 2010/0078553 A1 | 4/2010 | Corso et al. |

FOREIGN PATENT DOCUMENTS

| | | |
|---|---|---|
| WO | WO 2008/118808 | 10/2008 |
| WO | WO 2010/086179 | 8/2010 |
| WO | WO 2012/120102 | 9/2012 |

OTHER PUBLICATIONS

"8.3—Thin Layer Chromatography (TLC) Guide", MIT OpenCourseWare 5,301 Chemistry Laboratory Techniques, Jan. IAP 2012.*

"Overview of Mass Spectrometry for Protein Analysis," downloaded from https://www.thermofisher.com/us/en/home/life-science/protein-biology/protein-biology-learning-center/protein-biology-resource-library/pierce-protein-methods/overview-mass-spectrometry.html.html on Feb. 14, 2017.*

Balchen et al., "Electrokinetic Migration of Acidic Druqs Across a Supported Liquid Membrane", Journal of Chromatography, 2007, 1152(1-2), 220-225.

Lindenburg et al., "Online capillary liquid—liquid electroextraction of peptides as fast pre-concentration prior to LC-MS", Electrophoresis, 2010, 31(23-24), 3903-3912.

Pedersen-Bjersaard et al., "Electrokinetic Migration Across Artificial Liquid Membranes: New Concept for Rapid Sample Preparation of Biological Fluids", Journal of Chromatography, 2006, 1109(2), 183-190.

Petersen et al., "Drop-To-Drop, Microextraction Across a Supported Liquid Membrane By An Electrical Field Under Stagnant Conditions", Journal of Chromatography, 2009, 1216(9), 1496-1502.

Van Der Vlis et al., "Combined Liquid-Liquid Electroextraction and Isotachophoresis As A Fast On-Line Focusing Step in Capillary Electrophoresis", Journal of Chromatography, 1994, 687(2), 333-341.

Van Der Vlis et al., "Development of a Needle Device for On-Line Electroextraction-Liquid Chromatography", Journal of Chromatography, 1996, 741(1), 13-21.

Chye et al., "A Gel Elution Apparatus with High Sample Recovery", Analytical Biochemistry, 2000, 282, 258-259.

Lee et al., "Environmental and bioanalytical applications of hollow fiber membrane liquid-phase microextraction: A Review", Analytica Chimica Acta, 2008, 624, 253-268.

Lindenburg et al., "On-line large-volume electroextraction coupled to liquid chromatography-mass spectrometry to improve detection of peptides", Journal of Chromatography A, 2012, 1249, 17-24.

Petersen et al., "Electromembrane Extraction from Biological Fluids", Analytical Sciences, Oct. 2011, vol. 27, 965-972.

Zhu et al., On-line combination of single-drop liquid-liquid-liquid microextraction with capillary electrophoresis for sample cleanup and preconcentration: A simple and efficient approach to determining trace analyte in real matrices, Journal of Chromatography A, 2010, 1217, 1856-1861.

* cited by examiner

ELECTROEXTRACTION

CROSS-REFERENCE TO RELATED APPLICATIONS

This application is the National Stage of International Application No. PCT/NL2013/050285, filed Apr. 19, 2013, which claims the benefit of Netherlands application number 2008662, filed Apr. 19, 2012, and U.S. provisional application No. 61/635,428, filed Apr. 19, 2012, the disclosures of which are incorporated herein by reference in their entirety.

The present invention relates to a process and apparatus for the electroextraction of compounds from a sample.

BACKGROUND OF THE INVENTION

Solvent extraction processes using application of an electric field to enhance mass transfer from one phase into the other are commonly known as "electroextraction". When an electrical field is applied in a two-phase liquid—liquid system consisting of a low conductive organic phase and a highly conductive aqueous phase, charged compounds that are in the organic phase will migrate fast toward the aqueous phase. As the aqueous phase is entered, migration speed decreases dramatically, causing analyte concentration at the interface.

Originally, electroextraction had been developed as a purification technique in the field of chemical engineering to enhance product yields, see for instance U.S. Pat. No. 3,841,984 and U.S. Pat. No. 3,472,080. More recently, electroextraction has been adapted for analytical purposes, extracting compounds from an organic into an aqueous phase in capillary vessels, as disclosed for instance in J. Chromatogr. A 1994, 687, 333-341 and Electrophoresis 2010, 31, 3903-3912. While this generally is a very effective process, it requires the analytes to be dissolved in an organic phase, which limits the potential application to molecules having an appropriate solubility, and involves an extra diluting step in the analytical procedure, i.e. the mixing of the sample with an organic phase.

A different approach was disclosed in WO-A-2007004892. Herein a process is disclosed for the electro-assisted extraction of at least one ionized or partially ionized organic compound from a first hydrophilic donor solution through a liquid membrane comprising an immobilized organic solvent into a second hydrophilic acceptor solution. While this process may allow extracting aqueous analyte samples from a first into a second aqueous solution, the presence of the membrane will only allow a limited number of compounds to pass into the receptor solution due to the transport limitation associated with the liquid membrane, and the fact that the artificial liquid membrane discriminates the majority of endogenous compounds from a biological matrix, which is highly undesired in metabolomics. Yet further, the device is complex, and the membrane will need to be discarded after a single application. Accordingly, there remains a need to improve the efficiency of the electroextraction processes.

SUMMARY OF THE INVENTION

The present invention relates to a process for the extraction of analyte compounds from a sample comprising one or more analytes in a donor phase into an acceptor phase, comprising the steps of:

a) providing an electrically conductive donor phase comprising the compounds in a first electrically conductive solvent or solvent blend, and an electrode arranged in electrically conductive contact with the donor phase, b) providing an electrically conductive acceptor phase in electrically conductive contact with a second electrode; and c) providing an insulator phase fluid communication with at least one of the donor phase and the acceptor phase, wherein the insulator phase is immiscible with the donor phase and/or the acceptor phase, and (d) applying an electrical field between the first and the second electrode.

The invention further relates to a device comprising (i) an electrically conductive donor phase comprising the compounds in a first electrically conductive solvent or solvent blend, and an electrode arranged in electrically conductive contact with the donor phase, (ii) an electrically conductive acceptor phase in electrically conductive contact with a second electrode; and (iii) an insulator phase fluid communication with at least one of the donor phase and the acceptor phase, wherein the insulator phase is immiscible with the donor phase and/or the acceptor phase, and (iv) means for applying an electrical field between the first and the second electrode; and optionally, further analysis or separation means.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantageous, independently protectable constructions for which protection is hereby claimed. Embodiments of the invention are described in greater detail hereinafter relative to the drawings, wherein:

FIG. 1 depicts a Conductive pipette-tip (=second electrode, 1), the Acceptor phase (2), an insulator phase (3), a Donor phase (4), a First electrode (5) and a Voltage Source (6).

FIG. 2 depicts a Donor phase (7), an Acceptor phase (8), an Insulator phase 1 (9), a First electrode (10), a Voltage source (11), an Acceptor phase 2 (12), an Insulator phase 2 (13) and a Second electrode (14).

DETAILED DESCRIPTION OF THE INVENTION

Figure 1:
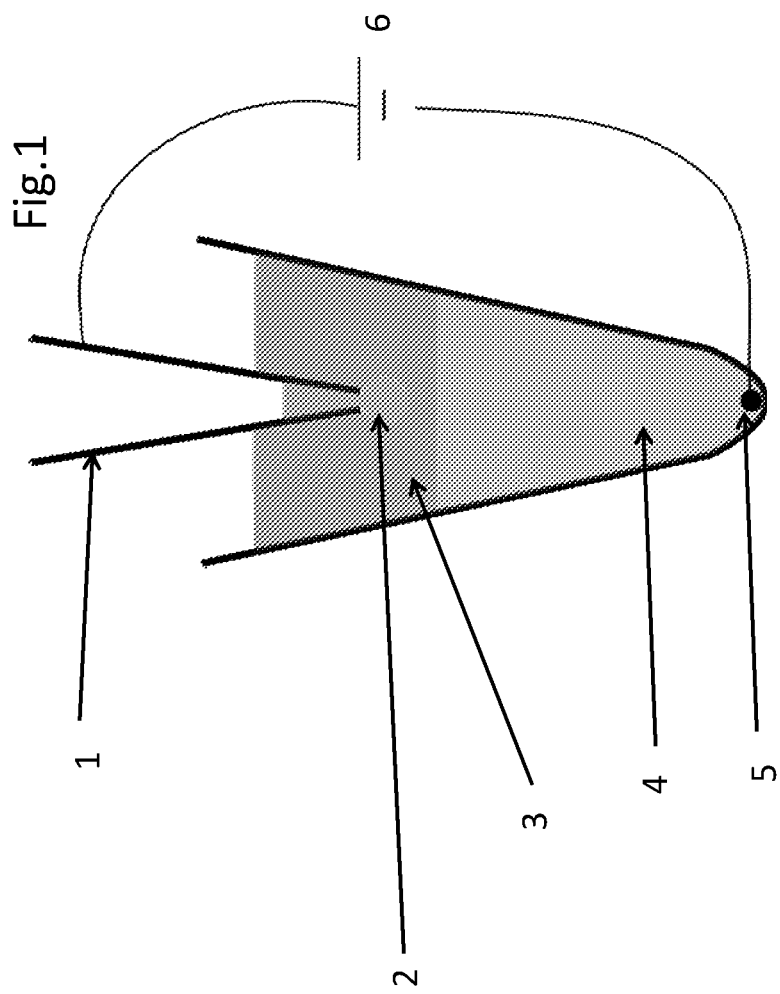
FIG. 1 discloses a schematic overview of the process line up, and a preferred device according to the present invention.

The phases employed in the subject process are to be understood as diluents that dissolve, or stably disperse or emulsify the analyte extractants and possible modifiers, thereby forming a phase.

The present invention relates to a separation performed by electroextraction, using three separate phases, namely a donor phase, an insulator phase, and an acceptor phase. The process may comprise further phases a suitable, provided the three phases are present.

The donor phase and/or acceptor phase according to the present invention may be any phase that is suitable for the dissolving and/or maintaining the analyte samples in a stable dispersion or emulsion. The donor, insulator and/or acceptor phase are preferably electrically conductive, more preferably in presence of the analyte samples, such as for instance an aqueous solution of salts. The phase may preferably comprise a single solvent, or a solvent blend.

The "electrically conductive" herein is to be understood as to provide sufficient conductivity to an electric field, i.e. a a current and said at least one analyte compound can traverse the phases, including the insulator phase. The electrical current that traverses the phases may in principle be any electrical current that does not give rise to instabilities that compromise the integrity of the interfaces between the phases. It is considered preferably that it should be in the lower microampere range, i.e. preferable less than 100 µA, but normally more than 0.01 µA.

The present process can be operated such that either positively or negatively charged compounds are extracted. While this may be achieved through switching polarity, or using two acceptor phases, one at each electrode, the process may also advantageously be conducted in absence of an electrical field, or wherein at least intermittently no field is applied to allow the migration of neutral analytes from the donor phase to the acceptor phase through fractional extraction. In this way, both charged as well as uncharged compounds may be extracted selectively, or sequentially.

Hence, the present process may also operate at least intermittently with no field applied to allow the migration of neutral analytes from the donor phase to the acceptor phase through fractional extraction.

Donor and/or acceptor phase are in electrically conductive contact with a first and a second electrode, respectively. This contact may advantageously be directly by having a fluid contact between the respective phase and electrode, or preferably through a further phase separating the electrode from the donor or acceptor phase. By this constellation, the occurrence of reduction or oxidation reactions between the analyte samples and/or solvent components, and the electrodes are avoided or at least reduced.

An insulator phase may for instance advantageously serve as way to bring the donor phase or acceptor phase into an electrically conductive contact with the electrode, thereby reducing the potential for undesired electrochemical reactions of analytes with the electrodes. Suitable electrodes may be any suitable, or commercially available electrode, such as for instance platina wires, a conductive metal coating or conductive plastics.

Preferably one or more of the electrodes are in electrically conductive contact with the donor/and or acceptor phase through a further insulator phase to avoid direct redox reactions.

The voltage applied to the electrodes may typically be in the range of 0.01V to 30000V; more preferably 0.1V to 10,000V, even more preferably 1V to 1000V, still more preferably 1 to 500V; and especially preferably 1V to 300V.

Preferably, the insulator phase separates the donor phase and the acceptor phase. Preferably, the insulator phase comprises hydrophobic solvents, and the donor and/or acceptor phase comprise hydrophilic solvents.

The applied voltage may preferably be a DC voltage. In some cases the applied voltage may be pulsed voltage. The polarisation of the voltage may depend on the analyte species to be separated, and may be varied.

Preferably the first electrode is arranged in a position distal to the insulator phase.

Preferably the donor and/or acceptor phase are hydrophilic, comprising solvents or solvent blends. Suitable solvents include aqueous solvents, nonpolar organic solvents such as dimethyl formamide (DMF) and dimethyl sulfoxide DMSO. The aqueous solvent used in the process according to the invention may be optionally a mixture of water and another solvent which is miscible with water and has a low solubility in the organic solvent of the insulator phase such that two separate phases are formed. A hydrophilic solvent may also comprise water in admixture with a hydrophilic organic solvent, wherein the organic solvent may be present in the range from 0-100% by weight; more preferably in the range from 0-50% by weight and still more preferred from 0-20% by weight. Further, suitable hydrophilic organic solvents may be added, which are preferably miscible with the donor or acceptor phase up to a certain level.

Examples of preferred hydrophilic organic solvents are methanol, ethanol, acetonitrile and DMSO.

The term "acceptor phase" as used in the context of the present application, is a phase suitable for accepting a compound.

At least the donor phase may preferably have a pH at which at least part of the analytes are partially or fully ionised. This can be achieved by addition of a suitable acid or base, as is well known in the art.

Suitable acids may be any acid that can adjust the pH of the donor solution to a level within the range of pH of 1 to 7, whereby an organic compound carrying a basic group is ionised to a cation. Correspondingly, a suitable base may be any base that can adjust the pH of the donor solution to a level within the range of pH of 7 to 14, whereby an organic compound carrying an acidic group is ionised to an anion. Examples of suitable acids are HCl, HBr, HCOOH, $CH_3COOH$, $H_2SO_4$ and $H_3PO_4$. Examples of suitable bases are NaOH, $Na_2CO_3$, $NaHCO_3$ and $NH_3$.

Suitable solvents also may include compressed gases, such as, for example, propane or carbon dioxide, which can be used in the subcritical, near-critical or supercritical phase range. To adjust the properties of these compressed gases, co-solvents such as, for example, ethanol, can optionally be added. Preference is given to using solvents which have no or only slight toxic or other physiologically disadvantageous effects. Further solvents may include silicon oils.

Further suitable solvents include ionic liquids. The term "ionic liquid" herein refers to salts that are liquid over a wide temperature range, including room temperature. Ionic liquids have been described in the art, including chiral, fluorinated, and antibacterial ionic liquids. Ionic liquid properties can tailored to specific applications, and may be environmentally-friendly alternatives to organic solvents. Ionic liquids can reduce the cost, disposal requirements, and hazards associated with volatile organic compounds. Exemplary properties of ionic liquids include at least one of high ionic conductivity, non-volatility, non-flammability, high thermal stability, wide temperature for liquid phase, highly solvability, and non-coordinating. The choice of cations and anions in the ionic liquids determine the physical properties, such as melting point, viscosity, density, water solubility and further properties of the ionic liquid. For example, big, bulky, and asymmetric cations may be employed, typically resulting in an ionic liquid with a low melting point. As another example, anions can contribute more to the overall characteristics of the ionic liquid, such as air and water stability. The melting point for ionic liquids can be changed by structural variation of at least one of the ions or combining different ions.

Examples of ionic liquid cations include, but are not limited to N-butylpyridinium and 1-alkyl-3-methylimidazolium (1,3-dialkylimidazolium; alkyl mim). Examples of anions include PF6 that is immiscible in water, and BF4– that is miscible in water depending on the ratio of ionic liquid to water, system temperature, and alkyl chain length of cation. Other anions can include triflate (TfO, $CF_3SO^{2-}$), nonaflate (NfO, $CF_3(CF_2)_3SO^{2-}$), bis(triflyl)amide, trifluoroacetate, and nonafluorobutanoate ($CF_3(CF_2)_3CO^{2-}$). Other examples of ionic liquids can include haloaluminates such as chloroaluminate. Chloro- and bromo-ionic liquids can have large electrochemical windows because molten salts prevent solvation and solvolysis of the metal ion species. Further examples of ionic liquids can include 1-alkyl-3-methylimidazolium PF6 such as 1-decyl-3-methylimidazolium PF6, 1-butyl-3-methylimidazolium PF6, and 1-ethyl-3-methylimidazolium with $NO_3$, $NO_2$, $MeCO_2$, $SO_4$, $PF_6$, TfO, NfO, $BF_4$, $Tf_2N$, and TA, N-alkylpyridinium chloride or N-alkylpyridium nickel chloride with $C_{12}$ to $C_{18}$-alkyl chains, and any variations of these as are known to one skilled in the art of ionic fluids. Other examples include 1-ethyl-3-methylimidazolium bis(1,2-benzenediolato-O,O')borate, 1-ethyl-3-methylimidazolium bis(salicylato)borate, 1-ethyl-3-methylimidazolium bis(oxalate)borate.

The insulator phase preferably has a dielectric constant in the range of from 1 to 40, determined at 25° C., such as preferably comprising ethyl acetate which has a dielectric constant of 6.0. The term "insulator phase" herein refers to a phase that in its broadest sense separates the donor and acceptor phase during the extraction process. This implies that the phases remain separate at least at the timescale of, and during the application of the extraction process.

This may conveniently achieved by immiscibility of the composition of the three phases under the process conditions, which is particularly suited for more static systems, or may be achieved at least in part by physical measures in dynamic systems, e.g. separating flowing phases by phase guides, as for instance disclosed in WO-A-2012120102 and/or WO-A-2010086179.

Such a system may advantageously be performed on a micro or nanoscale, e.g. using parallel lanes of fluid flows with an intermediate insulator phase flow, for instance on a microchip, preferably using phase guides to keep the flows immiscible.

Such systems are particularly useful when combining the process with an additional separation process prior to the electro extraction, which may advantageously also be performed automatically.

The main purpose of the one or more insulator phase(s) is to act as a phase boundary between the donor and acceptor phase physically during the extraction, while at the same time allowing the transport of molecules to be extracted to and/or through the phase interface.

Advantageously, the insulator phase is chose such that it increases the field strength over the phase, hence leading to significantly higher field strength at the interface with either donor and/or acceptor phase. Preferably, at least the donor and/or acceptor phase are aqueous phases, while the insulator phase comprises mainly one or more organic solvent(s), resulting in an organic phase.

The insulator phase according to the present invention preferably is essentially immiscible with either the donor phase, and the acceptor phase.

Accordingly, "Essentially immiscible" herein implies not mixing with, while being in direct contact with the acceptor and donor phase during the extraction process. "Essentially immiscible" herein advantageously may have the meaning that while the insulator phase may dissolve a certain percentage of the other phases, the thus formed solution will remain as a separate phase under the conditions of the process. In this invention it is understood that two solvents or solvent blends are immiscible when two separate phases form when the solvents or phases are mixed under the conditions of the process.

The insulator phase according to the present invention is essentially not supported by a membrane or any other contraption comprising hollow fibres. To the contrary, the insulator phase remains a fluid throughout the process, not being suspended or maintained in its position by a membrane or hollow fibre, and the phase separation is merely based on solubility under the process condition.

The insulator phase will have a sufficiently high conductivity in order to enable ion transfer of charged analyte compounds upon applying the electrical field. This may conveniently be achieved by e.g. saturation of the phase with one or more solvents that allow conductivity, e.g. by using ethyl acetate saturated with water as insulator phase. The saturation of the insulator phase with one or more solvents from the donor and/or acceptor phase also limits the loss of solvent from the acceptor or donor phase.

Suitable solvents for use in the insulator phase depend on the properties and composition of the two other phases, i.e. the three phase system has to be maintained.

Where a polar and/or aqueous phase is employed as donor phase, suitable insulator solvents include, but are not limited to nonpolar to moderately polar solvents, such as, for example, linear or branched cyclic or acyclic alkanes or alkenes, e.g., propane, butane, pentane, hexane, heptane, cyclohexane, petroleum ether, which can optionally be substituted with halogens, in particular chlorine, cyclic or acyclic linear or branched ethers e.g., diethyl ether, tert-butyl methyl ether, tert-butyl ethyl ether, tetrahydrofuran; primary, secondary or tertiary alcohols, in particular alkanols; e.g. n-butanol, tert-butanol, cyclohexanol; esters of short-chain carboxylic acids with short-chain alcohols, e.g., ethyl acetate, butyl acetate, propyl acetate; ketones, e.g., acetone, methyl isobutyl ketone; aromatic solvents, e.g. toluene and xylene, and mixtures of at least two of the above solvents.

Where at least the donor phase, and particularly both donor and acceptor phases are aqueous phases, applicants found that esters of short-chain carboxylic acids with short-chain alcohols, in particular ethyl acetate, were found to be highly effective in extracting certain metabolites.

The choice of acceptor phase, insulator phase and donor phase depends on the according to the present invention depends on the separation process.

Figure 2:
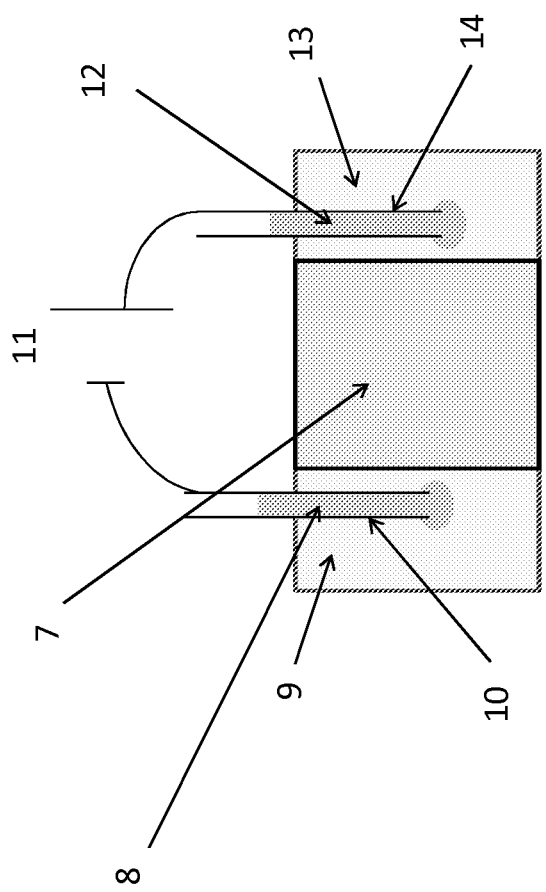
FIG. 2 discloses a further preferred embodiment of the process wherein two acceptor phases are present.

The present invention is not limited to a three-phase system, but the system may comprise further phases. A preferred embodiment comprises at least a further insulation phase comprising the electrode, wherein this phase is in electrically conductive contact with the donor or acceptor phase. In a further preferred embodiment, the insulator phase comprising the electrode is in electrically conductive contact with the acceptor phase, while the donor and the acceptor phase are in direct fluid contact with each other. FIG. 1 depicts such a system; in FIG. 2, two acceptor phases are arranged in a single donor phase, whereby the two acceptor phases also are in contact with the two electrodes.

In yet a further preferred embodiment, each electrode is formed in such manner as to comprise a separate acceptor phase, e.g. in a capillary vessel, thereby leading to an enrichment of both cationic and anionic analyte species in the respective acceptor fluids.

The present process may be directed at extraction of cationic analyte species, anionic analyte species, and advantageously, also neutral species. In the latter case, the separation through the insulator phase is performed without applying a field, and thus simply based on fractionation extraction.

Without wishing to be bound to any particular theory, it is believed that the small acceptor phase volume may allow removing compounds selectively from the donor phase, even without an electric field, although the latter increases the efficiency of the process significantly. The fractionation extraction may advantageously be optimized by optimizing the surface to volume ration of the phases, for instance in microfluidic chips.

The ionisation of the analyte compounds may be achieved by pH adjustment, by addition of a complexing agent, e.g. borates for carbohydrates (sugar) metabolites, or simply by application of a sufficiently high current over the electrodes. The insulator phase preferably functions as a filter phase, ensuring the filtration of proteins, and to remove dust at the phase interface.

The insulator phase may advantageously be tuned to achieve a desired selectivity for certain analytes. This may be advantageously be achieved by varying the composition of the insulator phase. The insulator phase may further comprise additives such as ion pairs that may act as phase transfer catalysts, or to increase polarity up to desired level.

The electrical field may also be alternated or alternating.

Examples of analytes that may be separated by the present process include organic compounds, such as pharmaceuticals, drugs, colouring agents, poisons, pollutants, food additives and metabolites; nucleotides such as DNA or RNA; proteins, peptides, amino acids, carbohydrates, lipids, polysaccharides fatty acids and phospholipids. Applicants have found that due to the difference in solubility between the donor phase and the insulator phase, e.g., the transfer of larger, highly charged molecules may be impeded, allowing to concentrate smaller and more mobile compounds in the acceptor phase selectively.

The donor phase may be a sample taken directly from a biological source, wherein the analyte compounds is already in a dissolved state. This may for instance be a sample from one of the biological fluids of a person, a water sample from drinking or wastewater, beverages, a sample from a preparative or industrial biochemical, organic or fermentation process. Examples of biological samples are blood, serum, urine, *salvia*, sputum, semen, cell lysate, embryo lysate, cell fluid, breast milk or spinal fluid. Other samples include the fractions of separation methods, for instance LC or HPLC.

The present process preferably is executed in a manner such that either the donor phase, or the acceptor phase are transportable, i.e. that they can be removed from the system. An example for this is the use of a capillary vessel comprising the acceptor fluid in the lumen of the vessel, whereby the vessel is in fluid communication with the insulator phase. Preferably, the acceptor phase is comprised in the lumen and/or a droplet at the tip or in the lumen of a tubular capillary vessel.

This vessel may comprise one or more of the phases employed. Upon transfer of the components from the donor phase, the acceptor phase enriched with the components can be advantageously simply removed from the insulator phase by removal of the capillary vessel. As a result, the thus obtained enriched acceptor fluid may then be subjected directly to a further separation of analysis or separation step e.g. when using the concentrated droplet for mass spectroscopy. Suitable further separation and/or analytical methods include, but are not limited to LC such as RP, NP, TLC; CE, NMR, MS, UV/VIS, ED, nano LC, HPLC, UPLC; RP-(UV/VIS)-EV-NP-MS; LC-EV-MS, RP-(UV/VIS)-EV-NMR; NP-(UV/VIS)-EV-CE-MS/RP-(UV/VIS)-EV-CE-MS; RP(UV/VIS)-EV-TLC/NP-(UV/VIS)-EV-TLC; EV-nano LC and CE-EV, of which MS is highly preferred. Preferred MS methods include multidimensional MS/MS or (MS)-ion mobility-MS, and coupled methods such as GC/MS or GC-MS/MS; in particular nanoelectrospray-Direct-Infusion-MS, such as those for instance disclosed in US-A-2010078553, or WO-A-2008118808, also known as Advion TriVersa (DI-MS); CE-MS; LC-MS; GC-MS and NMR.

The analytes entering the present process may also be the result of the above disclosed separation methods. The acceptor phase may be a deuterated phase where the enriched electro extracted sample may be subjected to an NMR process.

If a capillary vessel is employed to comprise the acceptor phase, the latter preferably forms a droplet at the phase border with the insulator phase.

A droplet as described herein refers to a meniscus, droplet sheet or a spherically shaped droplet. The droplet is a small element of liquid, bounded almost completely by free liquid/liquid surfaces with the exception of the surface boundary provided by the distal end of the tubular vessel.

The droplet is formed when liquid accumulates in the vessel in the case of a meniscus, or a pendant or standing droplet in the case of a tip of a tubular vessel or a droplet sheet in the case of for instance an elongated channel at the end of the vessel, as for instance provided by a channel in a microfluidic chip. If the vessel, the distal end of the vessel or the channel are pointing essentially downward, this will likely result in a pendant droplet, meniscus or droplet sheet, all of which will be referred to as "droplet" herein.

A pendant droplet is suspended from the end of a tube by surface tension. Alternatively, the droplet may be formed by pushing a liquid upward through an essentially upward pointing distal end of the capillary vessel, or vessel itself thereby forming a standing droplet.

If a droplet is supposed to be transferred to a receiving means, or if a droplet is supposed to be disposed off, the droplet preferably is a pendant, i.e. freely-hanging droplet, balanced by the equilibrium between upward tubular vessel and surface forces and downward gravitational forces and electrical forces due to the electric field. Droplets of up to 15 μL volume have been shown to successfully hang at a tubular vessel exit before gravitational forces become larger than the upward forces in absence of an electrical field.

However, the droplet may have a different, smaller volume. Preferably the droplet comprises of from 0.001 to 15.0 μL, more preferably of from 0.01 to 14.0 μL, yet more preferably of from 0.1 to 5.0 μL of liquid feed.

If the droplet is a pendant droplet, it will usually have a diameter of less than 500 μm diameter. The volume and the diameter are linked by a cubic function relative to the diameter: while a droplet with a 50 μm diameter represents a volume of 65 picoliters, a 500 μm diameter drop represents in 65 nanoliters volume.

In general, the present process permits to concentrate analytes from a larger donor phase into a mall acceptor phase, thereby leading to a concentration of analyte. The latter is important for methods that are not sensitive enough and hence employ the thus concentrated acceptor phase further, wherein the presence of solvents would be detrimental, e.g. to the resolution of a method, such as a separation method where a solvent exchange is required.

The droplet may have a spherical shape or a meniscus shape, or an elongated droplet sheet shape, or any shape between the three. The spherical shape is most preferred, since it has the advantage that the surface to liquid volume ratio is maximal, thereby maximizing the analyte extraction.

The device according to the invention preferably employs a first tubular vessel having as an outlet a distal end or a channel suitable for the formation of a droplet of a first volume.

The term "tubular" vessel herein refers to an essentially tubular structure that comprises an outer surface, an inner surface and a lumen at the inside of the structure. The cross-sectional shape of the tubular wall structure may be circular, or square, or of a non-specifically defined geometry. The specific geometry of the cross-section is not considered as relevant, provided that the tubular device is suitable for transferring fluids, such as for instance also applicable for channels etched in a microfluidic chip.

The tubular vessel preferably has a defined lumen in which the acceptor phase is present. Preferably, the tubular vessel is a capillary tube having an inner diameter of less than 5 mm, measured as the diameter between the largest distances. Suitable wall materials are essentially inert with respect to the solvents and/or the components carried in the liquid feed, and are further not deformed at the temperatures or conditions employed in the subject device. Typical materials include silicon, metals and/or alloys such as gold, copper or stainless steel, glasses and thermoset polymeric materials such as crosslinked epoxy resins, poly methyl methacrylate, cyclo-olefin (co)polymers, polyimide, fluoroethylene polymer and/or polycarbonate.

A preferred tubular vessel comprises an robotic pipettor which allows moving subject materials with hydrodynamic and/or electro-osmotic forces. The robotic pipettor preferably has a capillary having a lumen. An electrode is preferably attached along the outside length of the capillary and terminates in a electrode ring at the end of the capillary. By manipulating the voltages on the electrode and the electrode at a target donor phase to which the lumen is fluidly connected when the end of the capillary is placed into a material source, materials may be electrokinetically introduced into, and maintained in the lumen. The tubular vessel preferably is an electrically controlled micro-pipette or electropipettor, wherein the lumen is brought into an electrically conductive contact with the second electrode.

The acceptor phase is in electrically conductive contact with a second electrode. This may conveniently be achieved by a tubular vessel that is electrically conductive at least one point in contact with the acceptor phase, thereby forming the second electrode, e.g. by making the tip of vessel electrically conductive; or alternatively, bringing the acceptor phase into contact with an electrode in the lumen.

The sample may comprise dissolved components, or components that are suspended or emulsified in the donor phase.

The following examples illustrate the process and devices according to the invention:

Example 1

The experiments were performed in a device for electroextraction as illustrated in FIG. 1.

50 µL of a sample solution of 33% wt/wt MeOH in $H_2O$ with 0.1% formic acid, comprising 5 µM of an analyte mixture was filled into an Eppendorf vessel prepared from polypropylene, thereby forming the donor phase. A platina wire was placed into the bottom of the vessel in contact with the donor phase and connected to the power supply.

100 µL of ethyl acetate saturated with $H_2O$ was placed on top of the donor phase, acting as a insulator phase.

2 µl of 33% MeOH in $H_2O$ with 0.1% formic acid was drawn into the tip of a pipette, which served as the acceptor phase. The tip of the pipette was electrically conducting, and connected to a second, negative electrode connected to the power supply. The tip of the pipette was entered into the insulator phase, and a small droplet was formed in the insulator phase. Then a voltage difference of 200V was applied over the two electrodes for a period of 3 minutes, whereby the first electrode serves as anode; and the second electrode as cathode.

Seven carnitines with increasing size, decreasing electrophoretic mobility and increasing log P values were selected as model analytes (see Table 1).

TABLE 1

Carnitines with varying mass and log P values

| Analyte | Molecular weight (MW) | Log P* |
|---|---|---|
| Carnitine | 161.2 | −4.9 |
| Acetylcarnitine | 203.2 | −4.45 |
| Propionylcarnitine | 217.2 | −3.75 |
| Butyrylcarnitine | 231.3 | −3.30 |
| Hexanoylcarnitine | 259.3 | −2.41 |
| Octanoylcarnitine | 287.4 | −1.52 |
| Decanoylcarnitine | 315.4 | −0.63 |

*predicted by ChemAxon molconvert

Using these model analytes the dominant influence of log P of the analytes and thus the partition coefficients $K_1$ and $K_2$ in the 3-phase model could be demonstrated ($K_1$ being the partition coefficient between donor phase and insulator phase, and $K_2$ between insulator phase and acceptor phase).

The enrichment factor of the model analytes was studied as a function of 3-phase ethyl acetate time and voltage. Enrichment in this setup was achieved by extracting the analytes from 50 µL donor to a 2 µL acceptor droplet. As a consequence the theoretical maximum enrichment factor was 25. The carnitines were always charged, since they are quaternary ammonium compounds. The acceptor phase was spiked with 1 mM deuterated butyryl carnitine D3 which was used as an internal standard for normalization.

Experiments were performed with extraction times of 0.5, 1, 2, 3, 5 and 10 minutes at a voltage of 70 and 140 V. Applying an electrical potential difference of 140 V, several analytes were enriched close to the maximum enrichment factor already within 3 min.

The pipette comprising the acceptor phase droplet was then removed from the insulator phase, and the acceptor phase directly injected into a nanoelectrospray-Direct-Infusion-MS. The metabolites that were detected included alanine, cytosine, creatinine, valine, creatine, serine, leucine, adenine, hypoxanthine, tyramine, methionine, guanine, phenylalanine, tyrosine, tryptophan, adenosine, carnosine, carnitine, acetylcarnitine, hexanoylcarnitine, octanoylcarnitine and lauroylcarnitine which all could be extracted and detected successfully, and without the need to an additional purification or concentration step.

Example 2

In order to explore the depletion of the donor phase, three subsequent extractions were performed on the same donor and organic phase, refreshing only the acceptor phase after each extraction. The results showed that decanoyl and octanoylcarnitine were hardly present after the first extraction indicating that for these analytes the donor was almost depleted.

A comparative control experiment was conducted for transport based on 3 min of passive diffusion only, without applying the electrical potential difference. In this case none of the model analytes were detected. This proves that the transport speed from donor to acceptor phase was improved dramatically upon application of the voltage.

In the first 3 minutes the influence of both $K_1$ and $K_2$ is revealed, in that the most polar acylcarnitines, carnitine to hexanoylcarnitine, are extracted with an increased extraction rate (Δenrichment factor/Δextraction time) as the polarity of the analyte increases, imposed by $K_1$. These results confirm that the partition coefficient $K_1$ across the aqueous-organic filter interface is the limiting factor for this settings, since hexanoyl- and octanoylcarnitine were extracted faster than the smaller carnitines, while their electrophoretic mobilities are lower. For the most apolar carnitine, decanoylcarnitine, the extraction rate decreased with an increase in apolarity, which may be caused by the influence of $K_2$ becoming important for more apolar compounds.

These characterization results indicate that for each application with its associated target analytes an optimal organic filter phase may advantageously be employed.

Example 3

In this example, different organic insulator phase compositions were employed and the enrichment factor was calculated.

By mixing organic solvents and by adding an ion pair modifier, the polarity of the insulator phase, $K_1$, could be changed in order to tune selectivity of the 3-phase system. By adding an ion pair modifier, acting as phase transfer catalyst, e.g. DEHP, the organic filter phase became more accessible for ions, making $K_1$ more favourable towards polar analytes. Organic filter phases with increasing polarity were tested: ethyl acetate (EtoAC), EtoAC:MEtoAC (3:2), EtoAC+1% DEHP and EtoAC+5% DEHP.

The acceptor phase was spiked with 1 μM deuterated butyrylcarnitine D3 as an internal standard for normalization purposes.

Figure 5:
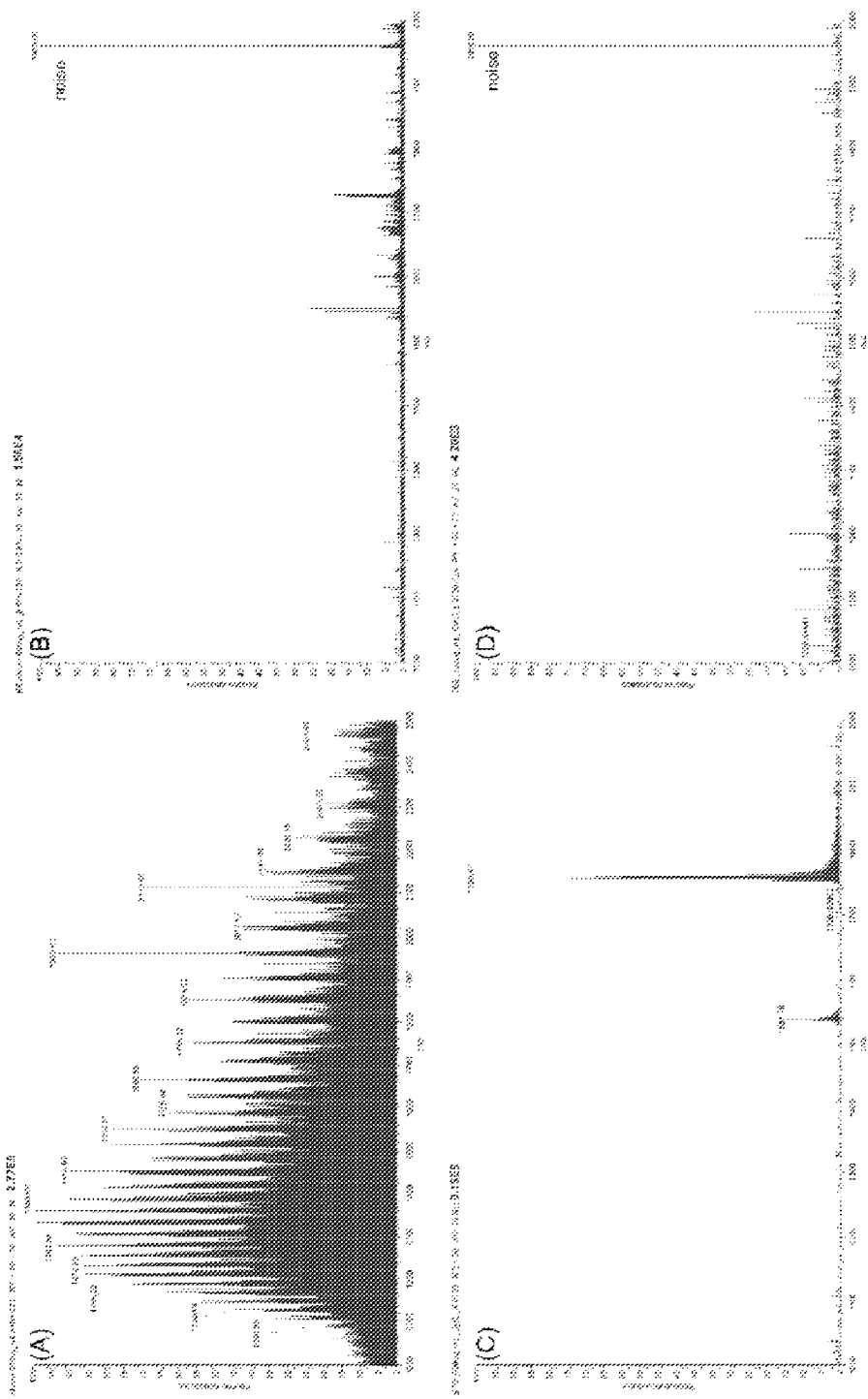
FIG. 5 discloses the averaged mass spectra of (A) BSA standard (500 µg/mL), (B) 3-phase Electroextraction (EE) of BSA standard (500 µg/mL); (C) Cyt C standard (500 µg/mL); and (D) 3-phase EE of Cyt C standard (500 µg/mL).

FIG. 5 shows that by increasing the polarity of the organic filter phase, the optimum log P shifts to lower values while seemingly narrowing the log P window, and hence increasing selectivity.

It could be observed that by using pure EtoAC the more apolar carnitines were most enriched, while transport of the smallest polar analytes was much slower at the same time due to the partition coefficient $K_1$. Accordingly, by adding 5% of the modifier DEHP, the extraction was more selective towards the polar carnitines and the largest, apolar decanoyal-carnitine was hardly enriched. These findings lead to the important conclusion that selectivity in 3-phase electro extraction system and process according to the present invention can be tuned. As a consequence, the selection of the composition of the insulator phase may be advantageously be tuned according the analytes of interest.

Example 4: Sample Purification

In the following experiments a test solution (500 mg/mL) of a large model protein BSA ($M_W$=66.5 kDa) and and a smaller model protein Cyt C ($M_W$=12 kDa) was tested. BSA was chosen because albumine is the most predominant (55%) blood plasma protein and cyt C was added to assess the behaviour of small proteins in the system.

The protein standard solutions were subjected to a 3-phase EE process coupled with DI-MS, and were compared to DI-MS of the donor phase before 3-phase EE to which 5% FA had been added. F FIG. 5a shows that the MS spectrum of the BSA standard consists of a broad BSA envelope centered around 1500 m/z, obtained for the analysis of the donor phase which is not observed with 3-phase EE-DI-MS (FIG. 5b). FIG. 5c show the MS spectrum of the Cyt C standard consists of two mailer envelopes centred around 1537 m/z and 1752 m/z, opposed to the MS spectrum of the 3-phase EE extract (FIG. 5d). These results show that the large BSA as well as the much smaller Cyt C are not transported into the acceptor phase during 3-phase EE. These results confirm the same selectivity principle (partition coefficient $K_1$) discussed in the previous paragraph: since the proteins do not dissolve (precipitation) in the used organic filter phase, they did not pass the donor-organic filter interface during 3-phase EE.

Example 5

Example 4 was repeated, however scanning the same mass range for the presence of proteins in spiked plasma. In these experiments protein precipitation was observed between the donor and organic filter phase.

The acyl carnitines were spiked into samples of a pool of human blood plasma. By spiking the carnitines the plasma was diluted 10× in 33% methanol and 5% FA (pH=2.0). Subsequently the samples were subjected to 3-phase EE with the same conditions as reported above. The model analytes were effectively extracted from human plasma.

These results show that 3-phase EE can be used for the enrichment of complicated samples. For all model analytes slightly lower enrichment values were obtained from human serum samples compared with those of standard solution. This may possibly be explained by the plasma protein binding of the model analytes.

Many other plasma components were observed in the spectra and by putative identification, based on exact mass, among others, several amino acids were annotated. Accordingly the present process and device appears particularly suitable for the analysis of many amino acids, more particularly for biological samples, such as for instance blood plasma, stool, blood, soliva or other samples comprising metabolites as analytes.

Additionally, for every calibration point in the calibration curve the mass range of 500-2000 m/z was scanned for proteins. The 3-phase EE extracts did not show significant peaks or envelopes that indicated the presence of proteins, opposed to the analysis of the donor phase before 3-phase EE. This confirmed that transport of proteins to the acceptor phase during 3-phase EE was prevented, thereby acting as a filter.

Example 6: Online 3-Phase EE-nanoESI-DI-MS

The 3-phase EE process according to the invention was integrated into a fully automated system using an automated nanoESI robot (Triversa NanoMate) were made. A 96 polypropylene well plate was modified by removing the bottom of some of the wells and replacing it by a stainless steel plate which functioned as the anode. The mandrel of the NanoMate, which grabs the pipette tip and which is also electrically connected to the grabbed pipette tip, functioned as the cathode. Both electrodes were connected to a voltage source. Manually 150 μL of the donor test mixture of 500 nM carnitines was pipetted in one of the wells containing a bottom electrode, followed by 250 μL of the organic filter phase on top. A sequence was programmed in the NanoMate Chipsoft software which 1) aspired 1 μL of the acceptor phase from a certain well, 2) moved the pipette tip to the extraction well in which it was positioned in the organic filter phase, 3) dispensed a 1 μL droplet and waited 3 minutes to perform the extraction, 4) subconsequently aspired the acceptor droplet back into the pipette tip and 5) performed nanoESI.

Figure 3:
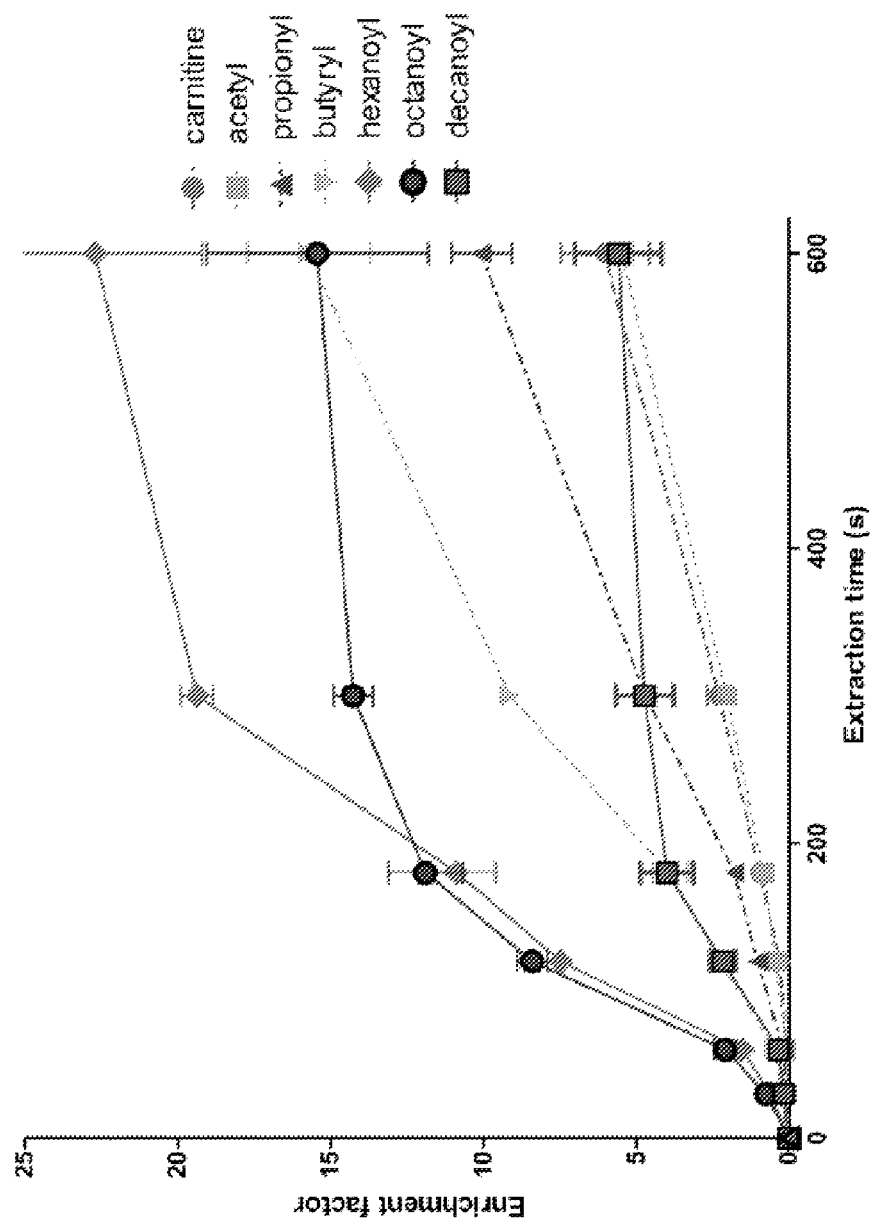
FIG. 3 discloses the average enrichment factor versus extraction time of the 7 model analytes applying 70 V.
Figure 4:
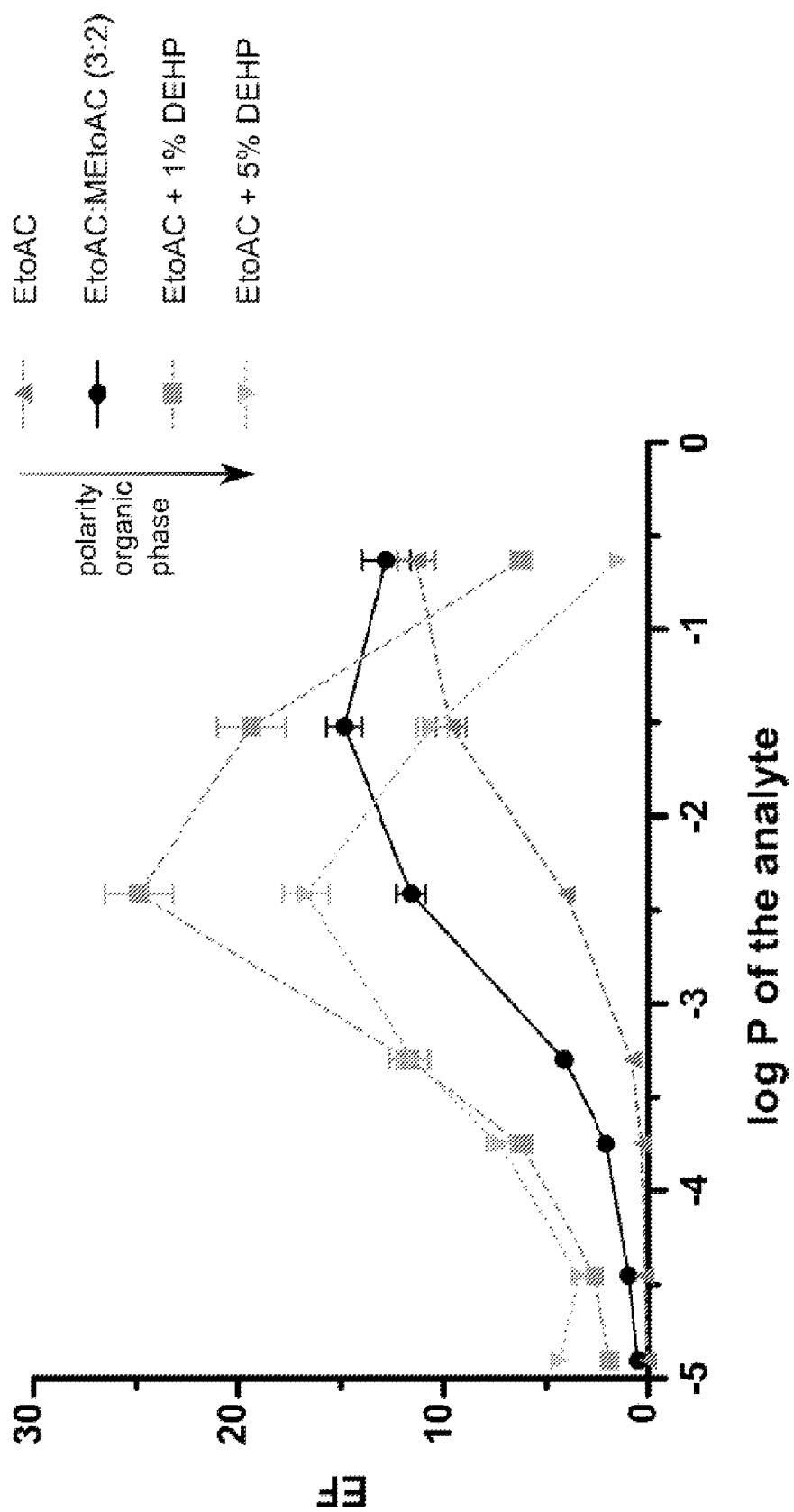
FIG. 4 discloses the average enrichment factor versus log P of the analyte and the influence of the organic filter phase ((n=3), all RSD<15%).

The needed extraction voltage was only 55 V in order to get the same extraction currents as the offline experiments and was manually turned on- and off using the external voltage source, but may also be automated. The results revealed an about 5-fold increase of the enrichment factor, compared to the offline results in FIG. 3. This increase in the enrichment factor can be explained by the 2-fold smaller acceptor volume and the 3-fold larger donor volume. This online result demonstrates that subject process may be operated in an automated, high-throughput sample preparation method, giving access to the use of a fully automated, high-throughput screening platform.

The above non-limiting examples illustrate the effectiveness of the subject process and device, in particular when coupled to a highly sensitive analysis method, such as nanoelectrospray-Direct-Infusion-MS.

The invention claimed is:

1. A process for the extraction of analyte compounds from a sample comprising one or more analytes in a donor phase into an acceptor phase, comprising the steps of:
   a) providing an electrically conductive donor phase comprising the analyte compounds in a first electrically conductive solvent or solvent blend, and a first electrode arranged in electrically conductive contact with the donor phase,
   b) providing an electrically conductive acceptor phase in electrically conductive contact with a second electrode; and
   c) providing an insulator phase in fluid communication with at least one of the donor phase and the acceptor phase, wherein the insulator phase is immiscible with the donor phase and/or the acceptor phase, and
   (d) applying an electrical field between the first and the second electrode;
   wherein the insulator phase remains a fluid throughout the process and is not supported or maintained in position by a membrane or hollow fibre.

2. The process of claim 1, wherein the insulator phase separates the donor phase and the acceptor phase.

3. The process of claim 1, wherein the insulator phase remains immiscible with the donor and acceptor phase during the time scale and under the conditions of the process.

4. The process of claim 1, wherein the insulator phase comprises hydrophobic solvents, and wherein the donor and/or acceptor phase comprise hydrophilic solvents.

5. The process of claim 1, wherein the first electrode is arranged in a position distal to the insulator phase.

6. The process of claim 1, wherein the acceptor phase is in a lumen of and/or in a droplet at a tip of the lumen of a tubular capillary vessel in fluid communication with the insulator phase.

7. The process of claim 1, wherein the electrical field is applied sufficiently high and in a sufficiently long period of time to allow at least part of the analyte compounds to migrate from the donor phase to the acceptor phase.

8. The process of claim 1, wherein one or more of the electrodes is in electrically conductive contact with the donor and/or acceptor phase through a further insulator phase.

9. The process of claim 1, further comprising removing the acceptor phase comprising migrated analytes, and subjecting the removed acceptor phase to a further separation and/or analysis process.

10. The process of claim 9, wherein the further separation and/or analytical process includes liquid chromatography (LC); CE, NMR, mass spectrometry (MS), UV/VIS, nano LC, high performance LC (HPLC), or ultraperformance LC (UPLC).

11. The process of claim 10 wherein said liquid chromatography is reverse phase, normal phase, or thin layer chromatography.

12. The process of claim 10 wherein said MS comprises multidimensional MS/MS, (MS)-ion mobility-MS, gas chromatography (GC)/MS, GC-MS/MS, or nanoelectrospray-Direct-Infusion-MS.

13. The process of claim 1, wherein the donor phase is the result of a further separation and/or analysis process.

14. A device comprising (i) a first vessel comprising a first electrode in electrically conductive contact with a donor phase, the donor phase being in the first vessel and comprising an electrically conductive solvent or solvent blend; (ii) a second vessel comprising a second electrode in electrically conductive contact with an acceptor phase, the acceptor phase being in the second vessel and comprising an electrically conductive solvent or solvent blend; (iii) an insulator phase in fluid communication with the donor phase and the acceptor phase, wherein the insulator phase is immiscible with the donor phase and the acceptor phase and is not supported by a membrane or hollow fibre; and (iv) means for applying an electrical field over the two electrodes, wherein the first and/or second vessel are moveable with respect to each other such that the phases may be brought into contact with the insulator phase.

15. The device of claim 14, wherein the second vessel is an electrically controlled micro-pipette or a robotic pipettor which moves subject materials with hydrodynamic and/or electro-osmotic forces.

16. A method for filtering proteins and/or removing dust from a biological sample, the method comprising applying the biological sample to the device of claim 14.

* * * * *